US00PP20208P2

(12) United States Plant Patent
Kordes

(10) Patent No.: US PP20,208 P2
(45) Date of Patent: Aug. 4, 2009

(54) MINIATURE ROSE PLANT NAMED 'KORFROSDRA'

(50) Latin Name: *Rosa hybrida*
Varietal Denomination: KORfrosdra

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/148,065

(22) Filed: Apr. 15, 2008

(51) Int. Cl.
*A01H 5/00* (2006.01)

(52) U.S. Cl. ..... Plt./118

(58) Field of Classification Search ..... Plt./118
See application file for complete search history.

*Primary Examiner*—June Hwu

(57) ABSTRACT

A new and distinct variety of miniature rose with long lasting, novel yellow flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfrosdra'.

BACKGROUND OF THE INVENTION

The new variety of miniature rose plant of the present invention originated from a controlled crossing in a breeding program between an 'un-named seedling' and 'KORmutric'.

The hybridization, seed production, seed germination, seedling selection, and subsequent propagations were conducted in controlled greenhouse environments. The new rose plant was selected as a single plant from the seedling beds due to its superior characteristics and asexually propagated for further evaluation. This new and distinctive miniature rose variety is named 'KORfrosdra'.

SUMMARY OF THE INVENTION

The new rose plant may be distinguished from its seed parent, an 'un-named seedling', by the following combination of characteristics:

1. The flower size of the 'un-named seedling' is large while the flower size of 'KORfrosdra' is medium, and
2. The flower color of the 'un-named seedling' is light yellow while the flower color of 'KORfrosdra' is yellow.

The new rose plant may be distinguished from its pollen parent, 'KORmutric' by the following combination of characteristics:

1. The flower size of 'KORmutric' is small while the flower size of 'KORfrosdra' is medium, and
2. The flower color of the 'KORmutric' is copper yellow while the flower color of 'KORfrosdra' is yellow.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers.

This combination of qualities is not present in prior rose cultivars. These objectives have been substantially achieved and in that distinguish 'KORfrosdra' from all other varieties of which we are aware.

As part of the rose development program, Tim-Hermann Kordes germinated the seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfrosdra' was selected in May, 2004 from the seedling beds to be asexually propagated for further evaluation. The first asexual reproduction of 'KORfrosdra' was done by rooting softwood cuttings in July, 2004 at the Rosa-Danica Nursery in Odense, Denmark.

This initial and other subsequent propagations conducted in controlled environments show that the foregoing and all other characteristics of 'KORfrosdra' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORfrosdra'. Specifically illustrated is: a flower bud, partially opened bloom, open bloom, floral parts, sepals, juvenile foliage, a stem exhibiting thorns, and leaves.

DETAILED BOTANICAL DESCRIPTION

The following is a description of 'KORfrosdra', as observed in its growth in April, 2008 in a greenhouse in Jackson County, Oregon on plants of 4 months of age. Color references are made using The Royal Horticultural Society (London, England) Colour Chart, 2001 except where common terms of color are used.

For a comparison, several physical characteristics of the rose variety 'KORspunty', a rose variety from the same inventor described and illustrated in U.S. Plant Pat. No. 17,402 and issued on Feb. 6, 2007 are compared to 'KORfrosdra' in Chart 1. ART 1

| | 'KORfrosdra' | 'KORspunty' |
|---|---|---|
| Bud color | Yellow-Orange Group 15C | Yellow Group 9A |
| Partially opened flower | Yellow-Orange Group 15C | Yellow Group 9A |
| General tonality | Yellow-Orange Group 14B | Yellow Group 9B |

Parents:

*Seed parent.*—An 'un-named seedling'.

*Pollen/parent.*—'KORmutric'.

Classification:

*Botanical classification.*—*Rosa hybrida,* 'KORfrosdra'.

*Commercial classification.*—Miniature rose.

FLOWER AND FLOWER BUD

Blooming habit: Recurrent.

*Flower bud.*—Size: Upon opening, 35 mm in length from base of receptacle to end of bud and 18 mm in diameter at its widest point. Bud form: Long and pointed ovoid. Bud color: As sepals first unfold, bud color is Yellow-Orange Group 15C. When ¼ open, the upper surface of petals is Yellow-Orange 15C, and the lower surface is Yellow-Orange Group 14B.

*Sepals.*—Size: Average 20–27 mm long×5–6 mm wide. Shape: Sepals generally subulate. Sepal apex is generally cirrose. Strong foliaceous appendages on three of the five sepals. Base is flat at union with receptacle. Quantity: Five. Margins: With occasional stipitate glands. Surface texture: Inner side: pubescent. Outer surface: smooth. Color: Upper surface: Green Group 138B. Lower surface: Green Group 138A. Intonations: Green-Yellow Group 1D and Green Group 143D.

*Receptacle.*—Surface: Smooth. Color: Yellow-Green Group 144A. Shape: Funnel-shaped. Size: 10 mm (h)×8 mm (w).

*Peduncle.*—Surface: Smooth. Length: 35–40 mm average length. Diameter: 3–4 mm average diameter. Color: Yellow-Green Group 144B. Strength: Somewhat strong. Borne: Singly.

Flower bloom:

*Fragrance.*—Light fragrance.

*Duration.*—Long lasting. A blooming plant with flowers has a commercial shelf life of 14–17 days. The blooms have a duration on the plant of approximately 11 to 14 days.

*Size.*—Medium for a 15 cm pot rose. Average flower diameter is 60–65 mm when open.

*Form.*—Shape of flower when viewed from the side: Upon opening, upper part: Flat. Upon opening, lower part: Flattened convex. Open flower, upper part: Flattened convex. Open flower, lower part: Concave.

Color:

*Upon opening, petals.*—Outermost petals: Outer Side: Yellow-Orange Group 15C. Inner Side: Yellow Group 13B. Innermost petals: Outer Side: Yellow-Orange Group 15B. Inner Side: Yellow Group 13B. No distinctive coloration at petal base observed.

*After opening, petals.*—Outermost petals: Outer Side: Yellow-Orange Group 13A with intonations of Yellow Group 8B. Inner Side: Yellow-Orange Group 14B. Innermost petals: Outer Side: Yellow-Orange Group 16B. Inner Side: Yellow-Orange Group 13B.

*After opening, basal petal spots.*—No distinctive coloration observed on outermost petals. Basal petal spot, innermost petals: Outer Side: Yellow Group 9A. Inner Side: Yellow Group 9A. Variegations: Occasional greenish streak on the guard petals. Color: Green-Yellow Group 1D.

General Tonality: On open flower Yellow-Orange Group 14B. No change in general tonality at the end of the $10^{th}$ day. Afterwards, general tonality is Yellow-Orange Group 14C.

Petals:

*Petal count.*—Approximately 25–30 petals under normal conditions.

*Petal reflex.*—Petals reflex slightly.

*Petal edge.*—Ruffled.

*Petal shape.*—Deltoid. Apex shape is round. Shape of base is rounded.

*Petal size.*—30 mm long; 35 mm wide.

*Thickness.*—Average.

*Petal arrangement.*—Generally in a regular pattern with overlapping edges.

*Petaloids.*—Present.

*Petaloid count.*—Average of 2–4 per flower.

*Petaloid edge.*—Undulated.

*Petaloid texture.*—Wrinkled and rough.

*Petaloid shape.*—Generally obovate. Linear to elliptic. Apex shape is round, and base shape is pointed.

*Petaloid size.*—Petaloids are 20 mm long and 10–15 mm wide.

*Petaloid color.*—Color of inner side is Yellow-Orange Group 14A. Color of outer side is Yellow-Orange Group 15B.

Reproductive Organs:

*Pistils.*—Approximately 25 present. Stigmas: Location: Inferior in position to anthers. Color: Green-Yellow Group 1B. Styles: Length: 4 mm long. Color: Green-Yellow Group 1D.

*Stamens.*—Approximately 45 on average and regularly arranged. Anthers: Size: 3 mm long. Color: Yellow-Orange Group 16A. Pollen: Absent. Filaments: Color: Yellow-Orange Group 17B. Length: 7–8 mm.

THE PLANT

*Plant growth.*—Moderately vigorous. Compact to bushy habit. When grown as a 15 cm pot plant, the average height of the plant itself is 26–28 cm and the average width is 24–26 cm.

*Stems.*—Stem color: Young wood: Yellow-Green Group 144C. Older wood: Green Group 138A. Stem surface: Young wood: Smooth. Older wood: Smooth.

*Prickles.*—Present. Incidence: 1 per 10 cm of stem. Size: Average length: 4 mm. Color: Immature prickles: Yellow-Green Group 154C. Mature prickles: Greyed-Orange Group 165B. Senescing to Greyed-Orange Group 166C. Shape: Linear. Anthocyanin: Not observed.

*Leaves and leaflets.*—Normally 5 leaflets on normal leaves in middle of the stem. Leaf size: 100–110 mm (1)×65–75 mm (w). Quantity: Average. Texture: Upper side of leaflet: Semi-glossy and smooth. Under side of leaflet: Matte and rough. Color, mature foliage: Upper Leaf Surface: Green Group 139A. Lower Leaf surface: Green Group N138C. Color, juvenile foliage: Upper Leaf Surface: Green Group 137B. Lower Leaf Surface: Green Group 138B. Anthocyanin intonation: Present. Location: Intonations present on leaf margins, rachis, and petiole of plants grown under high light conditions.

*Stipules.*—Size: 10 mm long. 6 mm between the tips of the stipule. Main body of stipule 5 mm in width. Shape: Longitudinally flanged or winged along middle. Stipule color: Yellow-Green Group 144B. Presence of stipitate glands: Located on margins. Margins: With stipitate glands.

*Petiole.*—Length: 15 mm–20 mm. Diameter: 1–1.5 mm. Petiole color: Yellow-Green Group 144A. Anthocyanin present on juvenile tissue. Color: Greyed-Purple Group 184A. Underneath: Smooth. Stipitate glands: Limited numbers of stipitate glands on margins.

*Petiole rachis.*—Length: 14–18 mm. Diameter: 1–1.5 mm. Color: Green Group 134B. Anthocyanin present on juvenile tissue. Color: Greyed-Purple Group 184A. Margins: With occasional stipitate glands. Prickles: Not observed. Stipitate glands: Limited numbers of stipitate glands on margins.

*Leaflets.*—Size: Average size of the terminal leaflet is 55 mm (1)×35 mm (w). Shape: Ovate. Base: Ovate. Apex: Acute. Surface: Upper side: Semi-glossy. Lower side: Matte. Margins: Finely serrated. Texture: Thin and rugose.

Hips/Seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to powdery mildew and *Botrytis* under normal growing conditions.

I claim:

1. A new and distinct variety of miniature rose plant characterized by the following combination of characteristics:

(a) Forms abundant, attractive long lasting yellow flowers;

(b) Exhibits a compact and bushy growth habit;

(c) Is suited for growing in greenhouse in pots from softwood cuttings, and;

(d) Exhibits durable flowers and foliage suitable for distribution in the floral industry; substantially as herein illustrated and described.

* * * * *

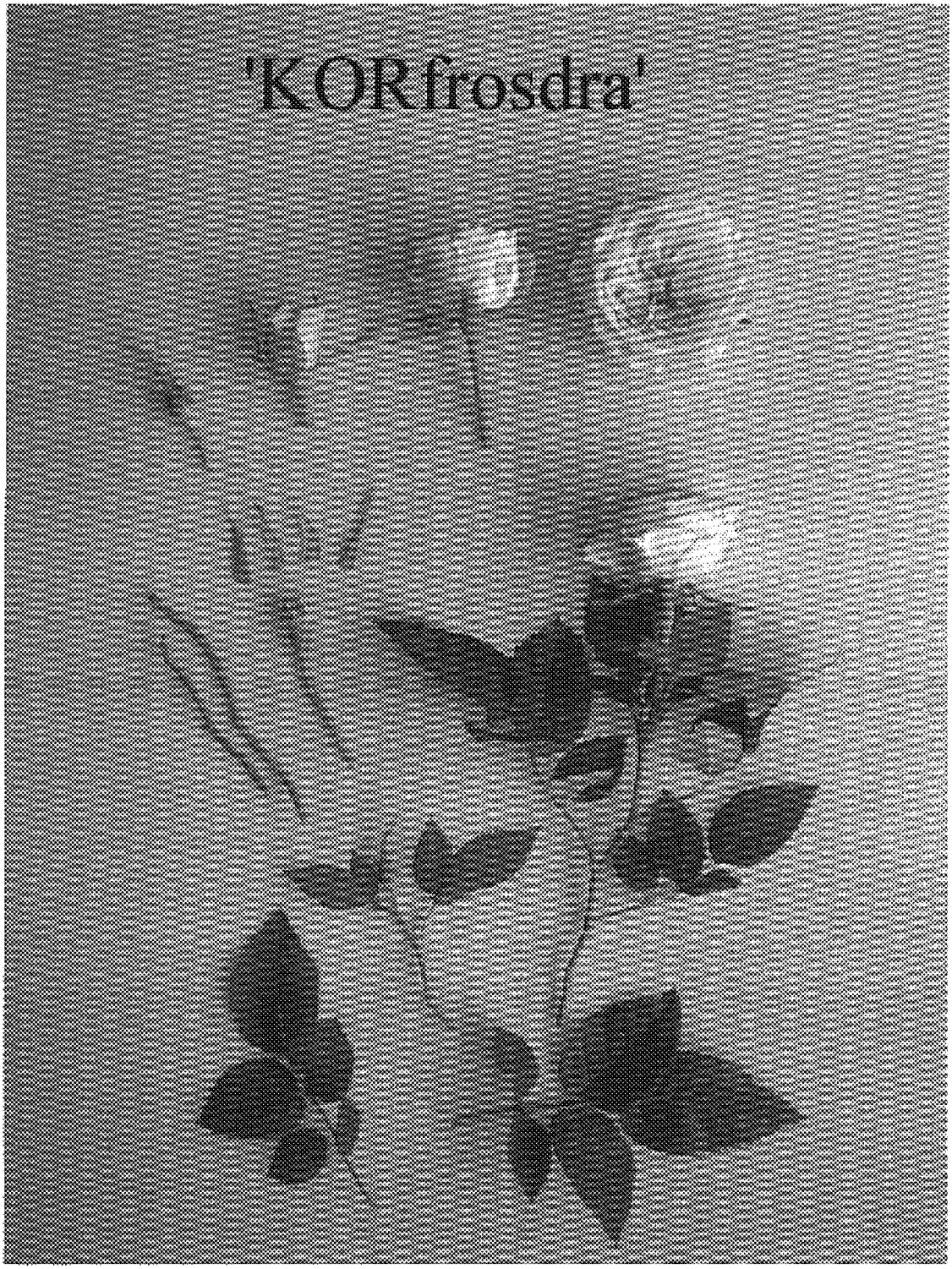
'KORfrosdra'